United States Patent
Göcking et al.

[11] Patent Number: 5,850,655
[45] Date of Patent: *Dec. 22, 1998

[54] ELECTRIC TOOTHBRUSH

[75] Inventors: Wolfgang Göcking, Frankfurt; Georges Driesen, Eschborn; Michael Drössler, Oberursel, all of Germany

[73] Assignee: Braun Aktiengesellschaft, Frankfurt, Germany

[ * ] Notice: The term of this patent shall not extend beyond the expiration date of Pat. No. 5,732,433.

[21] Appl. No.: 929,826

[22] Filed: Sep. 15, 1997

Related U.S. Application Data

[63] Continuation of Ser. No. 507,372, filed as PCT/EP94/00704 Mar. 8, 1994, Pat. No. 5,732,433.

[30] Foreign Application Priority Data

Mar. 20, 1993 [DE] Germany .......................... 43 09 035.4

[51] Int. Cl.⁶ ............................ A46B 13/02; A61C 17/34
[52] U.S. Cl. .............................. 15/28; 15/22.1; 15/DIG. 5
[58] Field of Search ................. 15/4, 22.1, 22.4, 15/28, 29, 167.1, DIG. 5

[56] References Cited

U.S. PATENT DOCUMENTS

| | | |
|---|---|---|
| 2,140,307 | 12/1938 | Belaschk . |
| 2,184,850 | 12/1939 | Schloss . |
| 2,625,697 | 1/1953 | Cyzer . |
| 3,177,509 | 4/1965 | Cyzer . |
| 3,676,218 | 7/1972 | Sawyer . |
| 4,356,585 | 11/1982 | Protell . |
| 4,845,795 | 7/1989 | Crawford . |
| 5,070,567 | 12/1991 | Holland . |
| 5,120,225 | 6/1992 | Amit . |
| 5,170,525 | 12/1992 | Cafaro . |
| 5,186,627 | 2/1993 | Amit . |
| 5,305,492 | 4/1994 | Givliani . |
| 5,467,495 | 11/1995 | Boland . |

FOREIGN PATENT DOCUMENTS

| | | |
|---|---|---|
| A 0259648 | 3/1988 | European Pat. Off. . |
| 528 920 | 7/1931 | Germany . |
| A 35 44 256 | 6/1987 | Germany . |
| A 39 37 850 | 5/1991 | Germany . |
| 2220845 | 1/1990 | United Kingdom . |
| 2247297 | 2/1992 | United Kingdom . |
| A 2 247 296 | 2/1992 | United Kingdom . |
| WO A 93 20777 | 10/1993 | WIPO . |

*Primary Examiner*—Randall E. Chin
*Attorney, Agent, or Firm*—Fish & Richardson P.C.

[57] ABSTRACT

The invention is directed to an electric toothbrush having a brush section and a drive shaft received in the brush section. The brush section includes a first bristle supporting structure operatively coupled to the shaft for motion about an axis essentially perpendicular to a longitudinal axis of the shaft, and a second bristle supporting structure operatively coupled to the shaft for substantially transverse oscillating motion of the entire second bristle supporting structure relative to the longitudinal axis of the shaft. The first bristle supporting structure is generally cylindrically shaped and carries a plurality of bristle clusters.

14 Claims, 3 Drawing Sheets

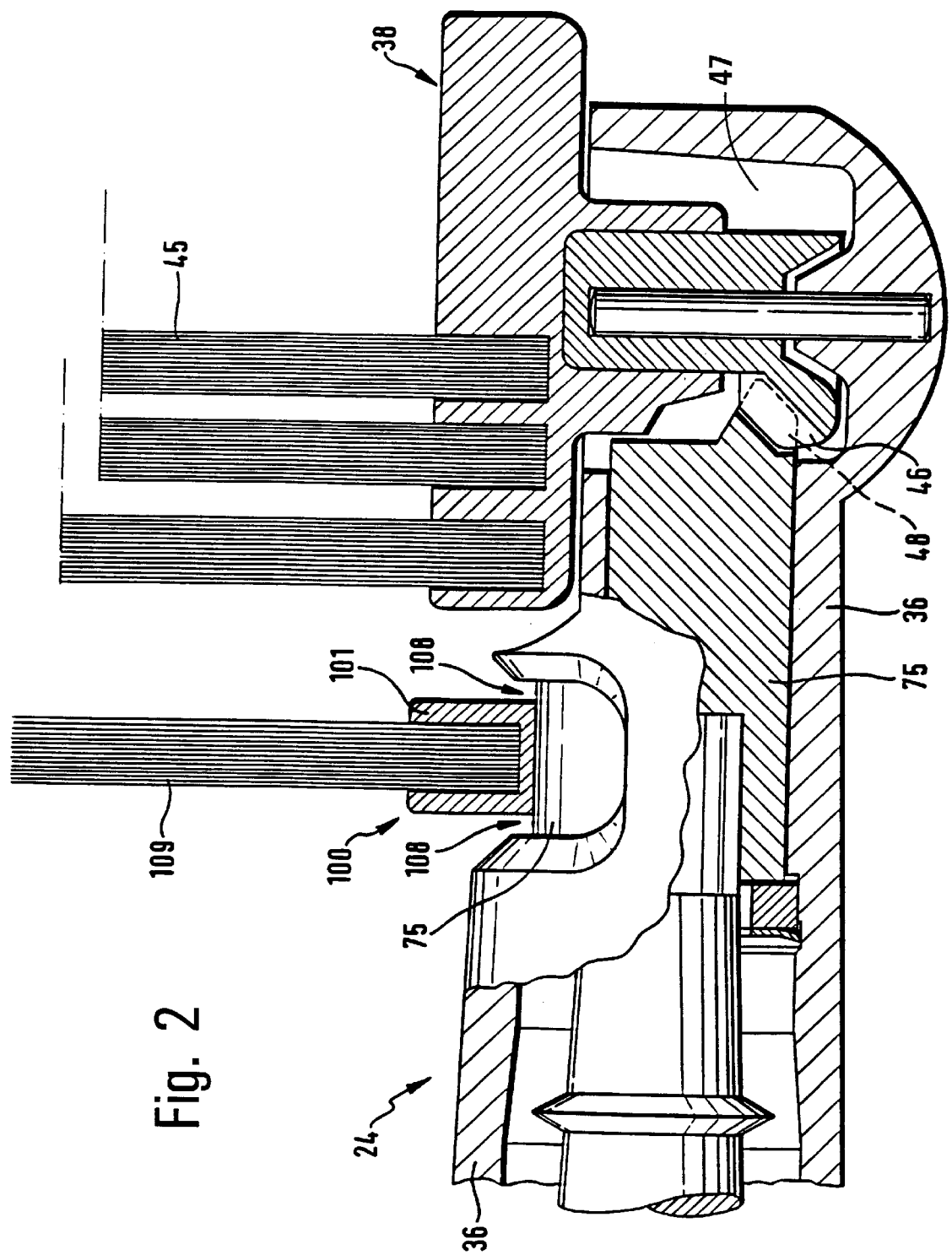

ELECTRIC TOOTHBRUSH

This is a continuation of application Ser. No. 08/507,372, filed as PCT/EP94/00704 published as WO Mar. 8, 1994 now U.S. Pat. No. 5,732,433.

BACKGROUND

This invention relates to an electric toothbrush, with a brush section in which a rotatably carried shaft is received and on which a bristle supporting structure coupled to the shaft is rotatably mounted, and with means for driving the shaft in an alternating motion.

An electric toothbrush of this type is known from German published patent application DE 39 37 850 A1 which is incorporated in the disclosure content of the present application by express reference. In this application, the alternating rotary motion of the shaft is transmitted to the bristle supporting structure by means of a bevel gear arrangement. The bristle supporting structure carries a plurality of bristles whose free ends form an approximately circular cleaning surface. With the electric toothbrush in activated condition, this cleaning surface performs an alternating rotary motion about its vertical axis. The operator of the toothbrush may use the cleaning surface for cleaning both the tooth surfaces and the interproximal spaces, in addition to massaging the gums.

From German design patent M 92 03 436 a push-on brush attachment for an electric toothbrush is known in which a bristle supporting structure is integrally formed with the stem of the brush. The bristle supporting structure includes a plurality of bristles whose free ends form an elongate cleaning surface, as well as a single bristle cluster whose bristles taper to a point. The cleaning surface essentially serves the purpose of cleaning the tooth surfaces, while the bristle cluster is intended for cleaning spaces between adjacent teeth. With the electric toothbrush activated, the movements produced by the bristles of the cleaning surface and the single bristle cluster are identical.

SUMMARY

It is an object of the present invention to provide an electric toothbrush of the type initially referred to with which an improved cleaning action, also of the interproximal spaces, can be accomplished.

This object is essentially solved by providing an interproximal brush which is coupled to the shaft independently of the coupling of the bristle supporting structure to the shaft.

Using an electric toothbrush of the type initially referred to, it is possible by means of the interproximal brush to clean interproximal areas particularly easily and thoroughly. However, rather than arranging the interproximal brush on the bristle supporting structure and coupling it to the shaft via the bevel gear arrangement, the interproximal brush is coupled to the shaft independently of the bristle supporting structure. It is thereby possible to impart a preferably alternating rotary motion about an axis substantially normal to the shaft to the bristle supporting structure, while imparting an alternating pivotal motion or reciprocating motion about the axis of rotation of the shaft to the interproximal brush. With the electric toothbrush in activated condition, the user is in a position to clean the tooth surfaces using the cleaning surface of the oscillating bristle supporting structure, in addition to cleaning the interproximal spaces using the interproximal brush that performs a pivotal or reciprocating motion. Cleaning of the teeth is thus essentially accomplished by means of the free ends of the bristles of the bristle supporting structure providing the cleaning surface, while the bristles of the interproximal brush are intended to perform a supplementary, still more efficient cleaning function of the interproximal spaces.

In an advantageous configuration of the electric toothbrush, the interproximal brush is arranged at a distance to the bristle supporting structure. This enables the interproximal brush to penetrate between adjacent teeth deeply, without the bristles that form the cleaning surface being in a position to prevent this from occurring due to their engagement against the tooth surfaces.

In a further advantageous configuration, the interproximal brush is disposed angularly, in particular at approximately right angles, with respect to the shaft. It is thereby accomplished that the interproximal brush performs a kind of wiping motion over a maximum possible surface, thus producing a superior cleaning action in the interproximal spaces.

Conveniently, the interproximal brush is arranged in the area of the brush section, with an opening being provided in the brush section through which the interproximal brush is passed. In this manner, access to the shaft accommodated in the brush section is not open, thus protecting the user of the electric toothbrush well from the possibility of injury by these components.

In an advantageous further feature of the electric toothbrush, the interproximal brush includes a mount in which at least one, in particular two bristle clusters are held. The bristle clusters are suitably arranged side-by-side in the direction of pivotal motion of the interproximal brush. By arranging bristle clusters in this manner, ease of penetration of the bristles of the bristle clusters between the user's teeth is accomplished.

The possibility exists to join this mount to the shaft by adhesive bonding or by welding to provide a nonrotative connection with the shaft. These methods present a simple and reliable way of fastening the interproximal brush to the shaft.

However, it is also possible in an advantageous manner to provide the mount with one or several trunnions and the shaft with one or several associated bores for fitting the mount therein. This type of coupling the interproximal brush to the shaft can be strengthened by the added provision of adhesive bonding or welding.

In another advantageous configuration of the electric toothbrush, the bristles of the bristle supporting structure extend approximately in the same direction as the bristles of the interproximal brush. Advantageously, the bristles of the interproximal brush are of greater length than the bristles of the bristle supporting structure. This enables the bristles of the interproximal brush to penetrate between the user's teeth with ease.

It has proven to be suitable to arrange for the shaft to rotate through an angular range of ±35 degrees, approximately. The pivotal range of the interproximal brush is thus of the same magnitude which ensures a good cleaning action.

In a still further configuration of the present invention, the mount has a bore in a base section thereof and is located in position on the shaft by means of a pin. This configuration has proven to be suitable particularly in an embodiment of the toothbrush as described in German patent application P 42 39 251. For one thing, this type of location enables the toothbrush to be assembled with ease, and for another thing, this type of location is highly economical.

By reason of the fact that the pin has one end received in a bore of the shaft and its other end in a bore of the mounting tube, with the bores being disposed concentrically with an axis of rotation of the shaft, the pin ensures an additional bearing function of the shaft in relation to the axis of rotation, aside from providing a locating function for the mount.

In a suitable further feature of the present invention, a rib structure arranged at the base section of the mount is received in a groove provided on the shaft. By this means, in particular in combination with the pin extending through the mount, the mount is located in position on the shaft in an extremely secure and lasting fashion.

In another advantageous configuration of the present invention, the bristle supporting structure has on its periphery a recess in the form of a circular segment. This affords the possibility of arranging the mount in very close proximity to, or even in the area of, the bristle supporting structure, thus providing in particular a highly compact and handy cleaning head of the brush.

Advantageously, the mount is disposed in the immediate vicinity of the bristle supporting structure and/or integrally formed therewith.

In a further feature of the present invention, the bristles of the mount have a larger diameter and/or a higher stiffness than the bristles of the bristle supporting structure. This increases the stability of the longer bristles of the interproximal brush to a sufficient degree, so that their penetration between the user's teeth is ensured.

Still further, the combined cleansing motions of the interproximal brush with the round brush have afforded the possibility of fixing the angle of rotation of the bristle supporting structure at values in the range of ±25 degrees, approximately. Owing to the cleansing action of the additional interproximal brush, the angle of oscillation of the bristle supporting structure can be reduced, thus enabling the expenditure for the gearing of the bristle supporting structure to be lowered. Another advantage resulting from reducing the angle of rotation of the bristle supporting structure is that the gearing is exposed to less severe loads than in cases where the oscillation angles are greater.

Further features, advantages and application possibilities of the present invention will become apparent from the subsequent description of embodiments illustrated in more detail in the accompanying drawings. It will be understood that any single feature and any combination of single features described and/or represented by illustration form the subject-matter of the present invention, irrespective of their summarization in the claims and their back-references.

BRIEF DESCRIPTION OF THE DRAWINGS

FIG. 2 is a longitudinal sectional view of the brush section of FIGS. 1a and 1b;

DESCRIPTION

The subsequent description relates to a further development of the toothbrush disclosed in German published patent application DE 39 3 850 A1 as well as of German patent application P 42 39 251.9 with an alternative gearing for the bristle supporting structure, whose disclosure content is incorporated in the present application by express reference.

Figure 1A:
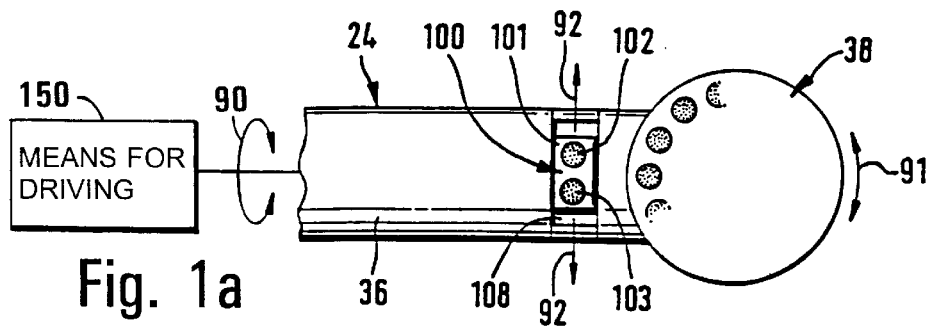
FIGS. 1a, 1b are, respectively, a top plan view and a side view, partly in section, of a brush section of an electric toothbrush illustrating an embodiment of the present invention in simplified form.
Figure 1B:
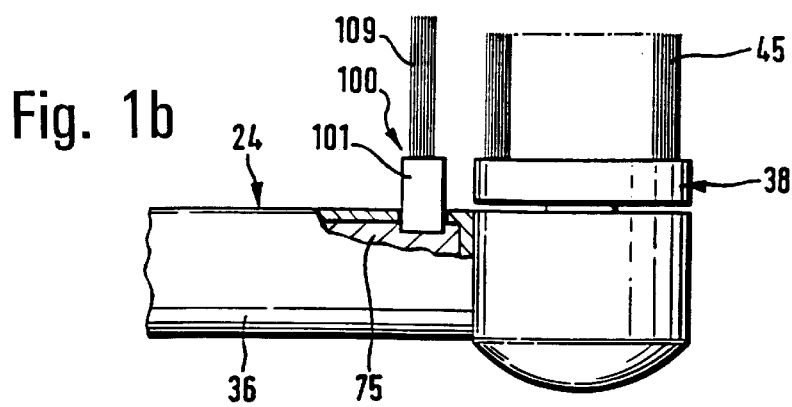
Figure 3:
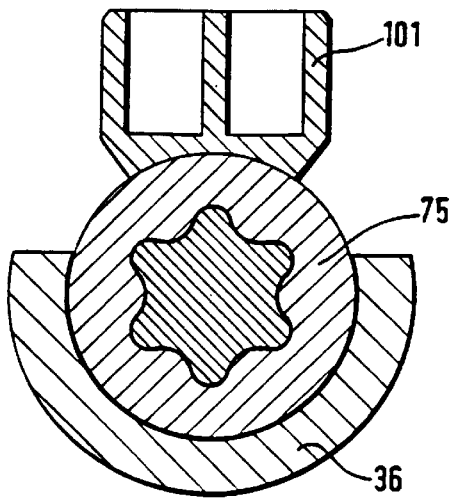
FIG. 3 is a cross-sectional view of the brush section of FIGS. 1a and 1b in the area of the interproximal brush, illustrating a first type of fastening.
Figure 4:
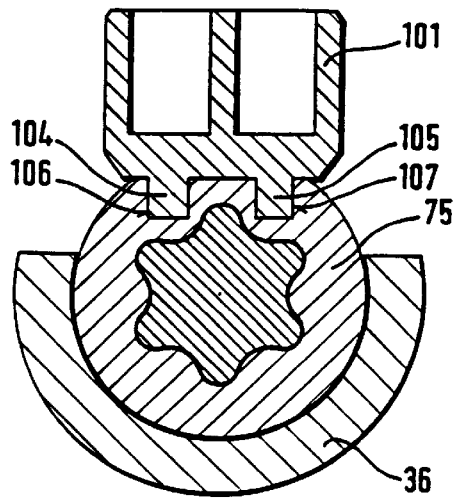
FIG. 4 is a cross-sectional view of the brush section of FIGS. 1a and 1b in the area of the interproximal brush, illustrating a second type of fastening.

FIGS. 1a and 1b of the present application illustrate schematically in a top plan view and, respectively, a side view a brush section 24 of an electric toothbrush of the invention. The brush section 24 is comprised of a hollow mounting tube 36 receiving rotatably therein a shaft 75. A bristle supporting structure 38 carrying bristles 45 combined into individual tufts is rotatably mounted at the free end of the brush section 24.

In a manner not shown, the shaft 75 is coupled to means 150 imparting an alternating rotary motion to the shaft 75 about the shaft longitudinal axis. The angular range through which the shaft 75 may be rotated is ±35 degrees, approximately.

Referring to FIG. 2, the axis of rotation of the shaft 75 and the axis of rotation of the bristle supporting structure 38 are preferably arranged at approximately right angles to each other. The bristle supporting structure 38 is provided with a bevel gear 47 meshing with a bevel gear segment 48 disposed at the head end of the shaft 75. This bevel gear arrangement provides for transmission of the alternating rotary motion of the shaft 75 to the bristle supporting structure 38. In FIG. 1a, the direction of rotation of the shaft 75 is identified by the reference numeral 90, while the direction of rotation of the bristle supporting structure 38 is designated by the reference numeral 91.

According to FIGS. 1a, 1b and 2, an interproximal brush 100 is arranged at a distance to the bristle supporting structure 38 and approximately in the area of the brush section 24. The interproximal brush 100 protrudes from the shaft 75 at about a right angle thereto, being fixedly connected with the shaft and extending outwardly through an opening 108 in the mounting tube 36. Neglecting the pivotal motion, the bristles 109 of the interproximal brush 100 extend in about the same direction as the bristles 45 of the bristle supporting structure 38. Further, the bristles 109 of the interproximal brush 100 are in particular about 1 to 2 mm longer than the bristles 45 of the bristle supporting structure 38.

The interproximal brush 100 includes a mount 101 in which the bristles 109 are held. The bristles 109 are combined to form in particular two bristle clusters 102, 103 disposed transversely to the shaft 75 in side-by-side arrangement.

In a first type of fastening, the mount 101 is joined to the shaft 75 by means of adhesive bonding or welding. In a second type of fastening, the mount 101 has on its underside two trunnions 104, 105 fitted into mating bores 106, 107 in the shaft 75. This second type of fastening the mount 101 to the shaft 75 may be further strengthened by the added provision of adhesive bonding or welding.

Being rotationally fixed relative to the shaft 75, the interproximal brush 100 performs an alternating pivotal motion about the axis of rotation of the shaft 75 when the electric toothbrush is activated, which motion is designated by the reference numeral 92. As the shaft 75 rotates in alternating directions, the interproximal brush 100 executes a wiper-type pivotal motion serving in particular interproximal cleaning needs. The alternating rotary motion of the bristles 45 of the bristle supporting structure 38 being used for cleaning substantially the outside surfaces of the teeth.

Figure 5:
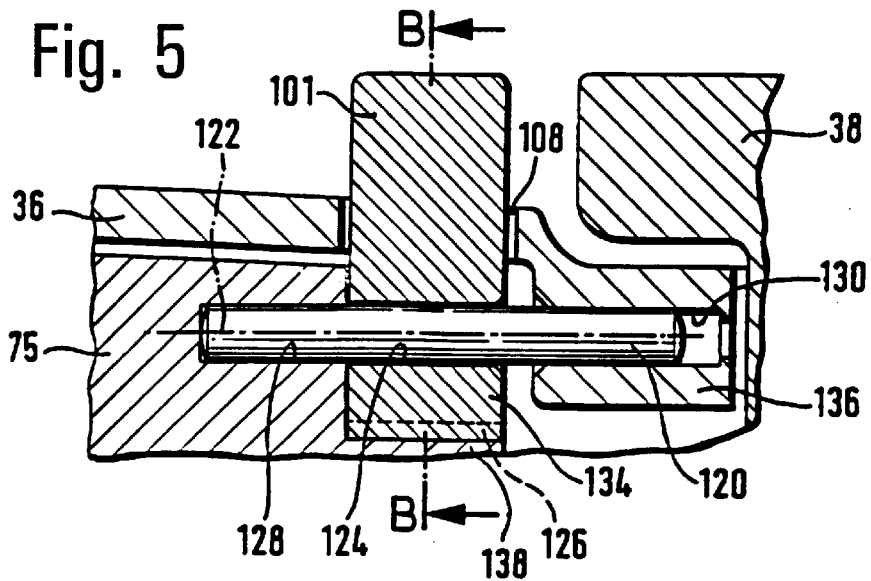
FIG. 5 is a partial longitudinal sectional view of the brush section in the area of the interproximal brush, illustrating a further type of fastening.
Figure 6:
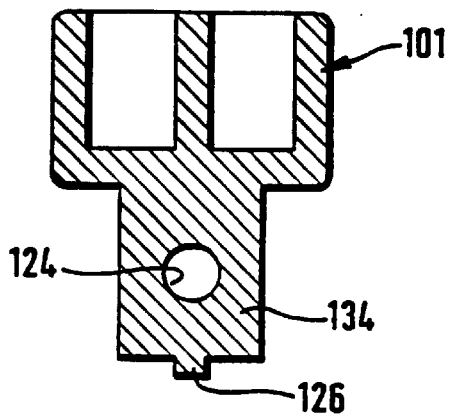
FIG. 6 is a sectional view of the mount of the interproximal brush, taken along the line B—B of FIG. 5.
Figure 7:
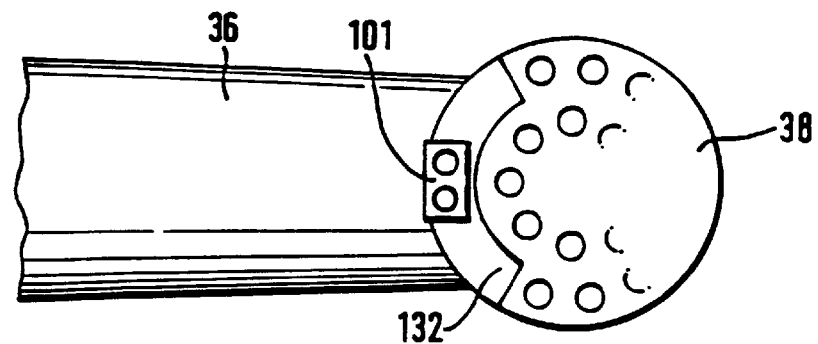
FIG. 7 is a top plan view of a further embodiment illustrated in simplified form.

In a further embodiment, the mount 101 is positioned in relation to the shaft 75 by means of a pin 120 (FIGS. 5, 6). To this end, the mount 101 has in a base section 134 thereof a bore 124. Further, a rib structure 126 may be disposed at the lower end of the base section 134. At its head end, the shaft 75 is provided with a bore 128, in particular a blind-end bore. A forward head section 136 of the mounting tube 36 includes equally a bore 130 which may also be configured as a blind-end bore. The center lines of the bores 128 and 130 are coincident with the axis of rotation 122 of the shaft 75. The head end of the shaft 75 may have an extension on one side in the form of a web member 138 including a groove, not shown in the drawings, in the axial direction for receiving, where applicable, the rib structure 126 formed on the base section 134. To mount the interproximal brush 100 on the brush section 24, the pin 120 is fitted into the bore 128, and the shaft 75 which is initially outside the mounting tube 36 is introduced into the open end of the mounting tube 36. The interproximal brush 100 is fitted into the opening 108 from above, and the shaft 75, together with the pin 120, is pushed in the mounting tube 36 in the direction of the head section 136. As this occurs, the pin 120 passes through the bore 124 in the base section 134 of the mount 101 and is received within the bore 130 in the head section 136 of the mounting tube 36. By this means, not only is the mount 101 fixedly secured in place on the shaft 75, but also a bearing of the head end of the shaft 75 is accomplished in relation to the axis of rotation 122.

According to a still further embodiment, the bristle supporting structure 38 may include a recess in the form of a circular segment 132 covering an angular range that corresponds approximately to the angle of oscillation of the bristle supporting structure 38. In the area of this circular segment 132, the mount 101 of the interproximal brush 100 is then arranged in the immediate vicinity of the bristle supporting structure. Due to such integration of the mount 101 in the area of the bristle supporting structure 38, a compact cleaning head having a single bristle cluster is obtained, in which a plurality of bristles 45 perform an oscillatory motion about the center line of the bristle supporting structure 38, while the bristles 109 of the interproximal brush 100 perform an oscillatory motion about the axis of rotation 122 of the shaft 75. Also in this embodiment, the bristles 109 of the interproximal brush 100 are of a longer configuration than the bristles 45. To enhance stability of the longer bristles 109, these are advantageously of a thicker configuration than the bristles 45 or are of greater stiffness as a result of the material selected.

We claim:

1. An electric toothbrush comprising:
   a brush section and a drive shaft received in said brush section, said brush section including
      a first bristle supporting structure operatively coupled to the shaft for motion about an axis essentially perpendicular to a longitudinal axis of the shaft, said first bristle supporting structure being generally cylindrically shaped and carrying a plurality of bristle clusters, and
      a second bristle supporting structure operatively coupled to the shaft for substantially transverse oscillating motion of the entire second bristle supporting structure relative to the longitudinal axis of the shaft.

2. The electric toothbrush as claimed in claim 1 wherein the second bristle supporting structure is arranged at a distance to the first bristle supporting structure such that the second bristle supporting structure cleans interproximally while the first bristle supporting structure cleans outside teeth surfaces.

3. The electric toothbrush as claimed in claim 1 wherein the second bristle supporting structure is arranged at approximately right angles with respect to the shaft.

4. The electric toothbrush as claimed in claim 1 wherein the second bristle supporting structure includes a mount in which at least one bristle cluster is held.

5. The electric toothbrush as claimed in claim 4 wherein the mount is disposed in the immediate vicinity of the first bristle supporting structure.

6. The electric toothbrush as claimed in claim 1 wherein the second bristle supporting structure holds bristles extending approximately in the same direction as the bristle clusters of the first bristle supporting structure.

7. The electric toothbrush as claimed in claim 1 further comprising the second bristle supporting structure holding bristles of greater length than the bristle clusters of the first bristle supporting structure.

8. The electric toothbrush as claimed in claim 1 further comprising means for driving the shaft in an alternating motion.

9. The electric toothbrush as claimed in claim 1 further comprising the second bristle supporting structure carrying a plurality of bristle clusters.

10. The electric toothbrush as claimed in claim 1 wherein the plurality of bristle clusters are arranged in only a single row.

11. The electric toothbrush as claimed in claim 1 wherein the second bristle supporting structure is directly coupled to the shaft.

12. The electric toothbrush as claimed in claim 1 wherein the shaft rotates about the longitudinal axis.

13. An electric toothbrush comprising:
   a brush section and a rotatably carried shaft received in said brush section, said brush section including a bristle supporting structure coupled to the shaft for motion about an axis perpendicular to an axis of rotation of the shaft, and
   only a single row of interproximal brushes coupled to the shaft.

14. The electric toothbrush as claimed in claim 13 wherein said interproximal brushes are spaced from said bristle supporting structure such that said interproximal brushes clean interproximally while said bristle supporting structure cleans outside teeth surfaces.

* * * * *